US006772762B2

(12) United States Patent
Piesinger

(10) Patent No.: US 6,772,762 B2
(45) Date of Patent: Aug. 10, 2004

(54) PERSONAL POWERED AIR FILTRATION, STERILIZATION, AND CONDITIONING SYSTEM

(76) Inventor: Gregory Hubert Piesinger, 6225 E. Saguaro Vista Ct., Cave Creek, AZ (US) 85331

(*) Notice: Subject to any disclaimer, the term of this patent is extended or adjusted under 35 U.S.C. 154(b) by 606 days.

(21) Appl. No.: 09/865,033

(22) Filed: May 23, 2001

(65) Prior Publication Data

US 2001/0050079 A1 Dec. 13, 2001

Related U.S. Application Data

(60) Provisional application No. 60/206,674, filed on May 24, 2000.

(51) Int. Cl.[7] .............................................. A61F 13/00
(52) U.S. Cl. .................. 128/847; 128/857; 128/200.14
(58) Field of Search ................................ 128/846, 847, 128/857, 858, 200.14, 201.24

(56) References Cited

U.S. PATENT DOCUMENTS 2,032,101 A * 2/1936 Sullivan .................... 128/847
3,747,599 A * 7/1973 Melmin ...................... 128/139
4,858,476 A * 8/1989 Tobin ...................... 73/863.23
5,878,742 A 3/1999 Figueredo et al.

* cited by examiner

*Primary Examiner*—Michael A. Brown

(57) ABSTRACT

Hollow eyeglass frames are combined with a wearable distributed air pump to form a portable positive pressure powered air purifying delivery system for inconspicuously supplying respirable air to the nostrils of an individual. Ambient air is pressurized by combining the outputs of a plurality of piston compression tubes arranged and connected to form a thin flexible pump that can be worn around the waist. This pressurized air is passed through filter and conditioning modules to form respirable air, which is then piped to air inlet ports on the hollow frame eyeglass temples using small diameter tubing. Nose tubes on the hollow eyeglass frames near the nose inconspicuously direct the respirable air into the nostrils at a rate that exceeds the peak inhalation rate of the individual, thereby preventing the inhalation of unfiltered air.

29 Claims, 9 Drawing Sheets

30
32
34
35
36
37
+v
-v

FIG. 4A
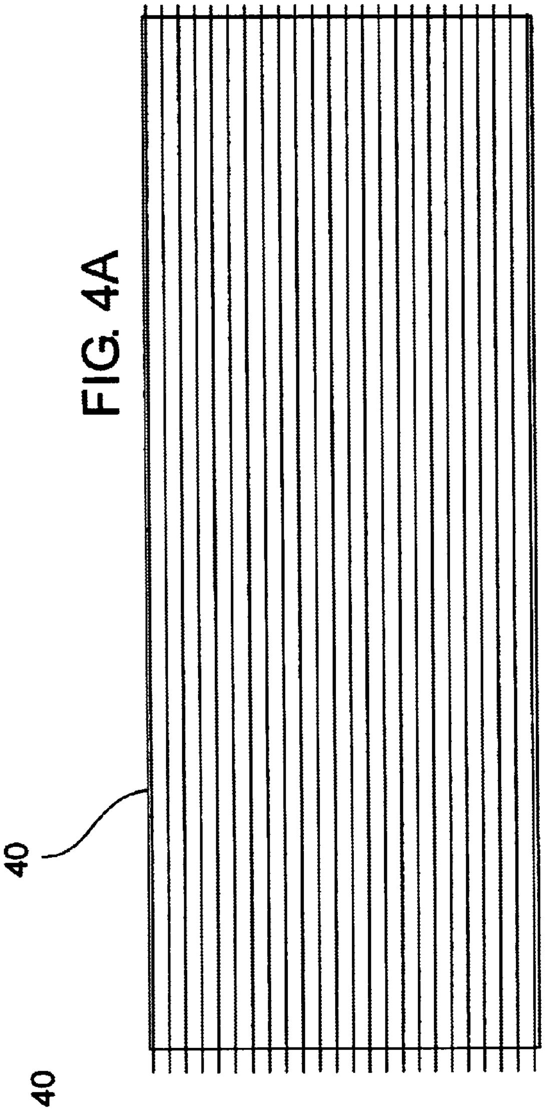
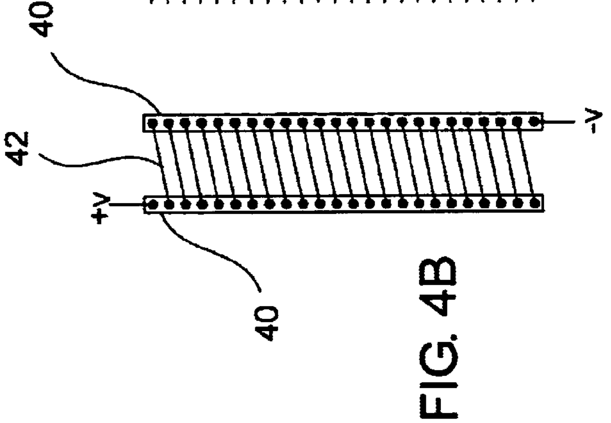
FIG. 4B
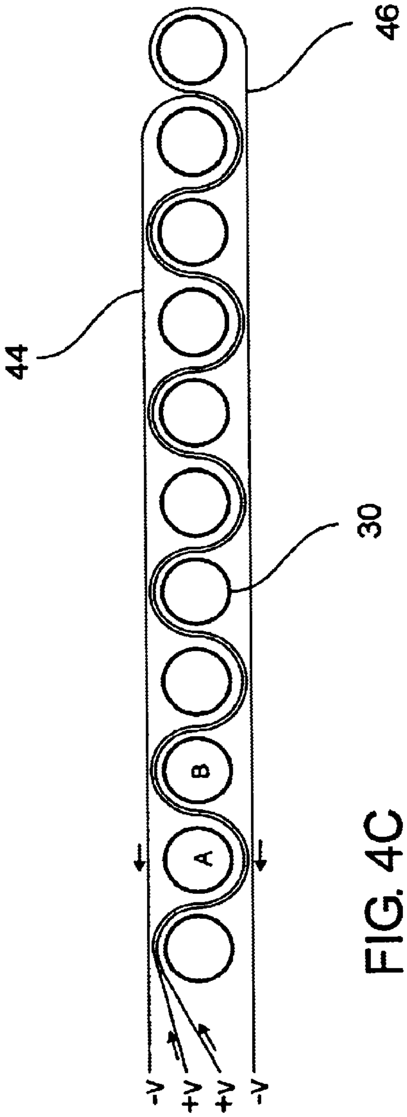
FIG. 4C

PERSONAL POWERED AIR FILTRATION, STERILIZATION, AND CONDITIONING SYSTEM

This application claims the benefits of Provision Application 60/206,674 filed May 24, 2000.

BACKGROUND

This invention relates to a non-obtrusive wearable positive pressure powered air filtration, conditioning, and sterilization system.

Devices for respiratory protection are readily available for industrial applications. The most common devices are negative pressure respirators which typically take the form of either a disposable mask or a half mask cartridge respirator. In either case, the mask covers the nose and mouth and air is drawn through the filter by the negative pressure of inhalation. These types of masks increase respiratory stress because the user must overcome the air restriction presented by the air filter. Facial hair also makes it hard to form a tight fit between the face and the mask. A tight fit is essential to prevent unfiltered air from entering around the mask instead of through the filter. These types of masks also interfere with normal conversation because they cover both the nose and mouth.

Also available, are positive pressure Powered Air Purifying Respirators (PAPRs) which use small battery operated motor and fan assemblies to draw air through the filter and supply it at a positive pressure to the user's face mask. These units eliminate respiratory stress and are not dependent on a tight fit between the face and mask. However, they also interfere with normal conversation because they are supplied with full or half masks that cover both the nose and mouth.

The problem with both these types of respirators are that they are not cosmetically appealing and are therefore seldom worn outside an industrial workplace.

However, there are many non-industrial situations in which respiratory protection would be highly beneficial. Allergy sufferers would greatly benefit from a pollen filter when outside during the allergy season as would people bothered by air pollution on high pollution days. Airline travelers would benefit from a cabin air ozone and germicidal filter, especially on long flights. Hospital workers and patients would benefit from germicidal filters. Finally, industrial workers would benefit from a less obtrusive respirator in non-toxic environments such as woodworking.

Although negative respirators could be worn in everyday non-industrial environments, they seldom are because of their obtrusiveness, respiratory discomfort, and difficulty in engaging in conversation. Currently available positive pressure PAPRs are large, noisy, and typically are supplied with full face masks. It would be extremely rare to see one of these units worn outside the workplace.

In summary, there are currently no acceptable devices for respiratory protection that are practical and cosmetically acceptable for use outside the industrial environment.

Figuereo, et al in U.S. Pat. No. 5,878,742 attempts to make a PAPR more appealing by disclosing a plenum arrangement near the forehead of the wearer along with a baffle for distributing the air from the plenum downward over the wearer's mouth, nose, and face. However, his device is still very large and obtrusive and would not appeal to users outside the workplace.

The primary problem with current portable PAPRs is that they are powered by fans or blowers. Fans and blowers can only supply very low static air pressures. This requires that large diameter hoses and large surface area air filters be used so as to not overly constrict the airflow from the blower. Typical hose diameters between a belt mounted blower and the face mask are one inch or larger.

Another problem with current negative respirators and PAPRs is that they are all designed to cover both the nose and mouth. However, covering only the nose would be perfectly acceptable in many non-toxic environments. For example, an allergy sufferer breathing filtered air through the nose would not be bothered by an occasional breath of unfiltered air through the mouth.

Yet another problem with both negative respirators and PAPRs is that they are only designed to filter the air and not to sterilize or condition it.

Accordingly, it is the object of the present invention to provide a new personal positive pressure powered respiratory protection system that would be cosmetically acceptable to the average user in an everyday environment.

Another object of the invention is to provide a system that can be easily configured for different filtering situations by offering various types of air filtration, sterilization, and conditioning capabilities using standard plug-in modules. Typical types of air filtration that will be provided are particulate, odor, ozone, and selected organic and chemical vapors. Sterilization will be provided using ultra-violet germicidal lamps. Typical air conditioning provided will be heating, cooling, or moisturizing the filtered air.

Still another object of the invention is to provide a distributed air pump that can be worn by the user as a wide thin belt.

Yet another object of the invention is to make the whole system portable, wearable, and concealable.

SUMMARY

Briefly, to achieve the desired objects of the present invention, a small battery powered air compressor capable of supplying the required airflow at pressures of several pounds per square inch (psi) will be provided so that small diameter hoses and small air filters can be used.

Hollow eyeglass frames will be provided to route filtered air from a small diameter air hose behind the head to small diameter nose tubes mounted on the bottom of the eyeglass frame rims near the nose. These short small unobtrusive tubes will curve upwards into the nose and deliver the filtered air directly into the nostrils. Small air outlet holes will be placed around the inside peripheral of the hollow eyeglass frame rims to supply filtered air to the eyes.

A distributed pump, composed of many small compression tubes, will be provided so as to form a thin concealable unobtrusive unit that can be worn around the waist.

A modular system design will be provided to allow the user to easily select various air purification, sterilization, and conditioning configurations by simply plugging in different filter modules.

Particulate filtering will be provided using HEPA (high efficiency particulate air) filters. Odor and ozone filtering will be provided using activated carbon, cpz (carbon, permanganate, and zeolite), or the like. Organic and chemical vapor filtering will be provided using readily available filters custom packaged for this system. Air sterilization will be provided using an ultraviolet germicidal lamp. Air conditioning will be provided using a distilled water moisturizing module for humidifying, a solid state thermoelectric cooler module for cooling, and a resistive element for heating.

In its most concealable form, the pump, filters, battery pack, and other modules will be mounted on a wide thin belt that can be worn around the waist under the clothes. In other optional forms, the system will be supplied in a small travel pack or bedside pack.

DRAWINGS

FIG. 1 illustrates the hollow eyeglass frames and nose tubes. FIG. 1A shows a user wearing the eyeglasses. FIG. 1B shows various parts of the eyeglasses. FIG. 1C shows an optional shroud that can be used when providing filtered air to the eyes.

FIG. 2 illustrates the routing of the air hose to the hollow eyeglass frames. FIG. 2A shows both eyeglass temples being supplied with filtered air. FIG. 2B shows a single temple being supplied with filtered air.

FIG. 3 illustrates a single compression tube of the distributed pump. FIG. 3A shows the movement of a piston when energizing a coil of wire with positive polarity. FIG. 3B shows the piston movement using negative polarity. FIG. 3C shows piston movement using multiple coils of wire.

FIG. 4 illustrates how multiple-wire cable can be used to form the compression tube coil. FIG. 4A shows the construction of multiple-wire cable. FIG. 4B shows how the cable can be wired to form a coil. FIG. 4C shows how two sections of cable can form a coil around a series of compression tube.

FIG. 5 illustrates how the compression tubes can be connected together to form a distributed pump. FIG. 5A shows the air flow while energizing the coil with positive polarity. FIG. 5B shows the air flow while energizing the coil with negative polarity.

FIG. 6 shows a perspective view of the air filtration system mounted on a wide thin belt designed to be worn around the waist of the user.

FIG. 7 illustrates a few of the various filtering, sterilization, and conditioning modules that can be used to configure the system. FIG. 7A shows a basic HEPA filter module. FIG. 7B shows a filter module using both activated carbon and HEPA filters. FIG. 7C shows a sterilization module. FIG. 7D shows a moisturizing module.

DETAILED DESCRIPTION

The goal of the present invention is to provide a quiet lightweight personal air filtration system that can be totally concealed on the person and does not interfere with the user's normal activities such as speaking, dining, traveling, etc. The user breaths normally through the nose without any restrictions.

To achieve these goals, filtered air at positive pressure is delivered directly to the nose in a non-conspicuous manner.

Figure 1B:
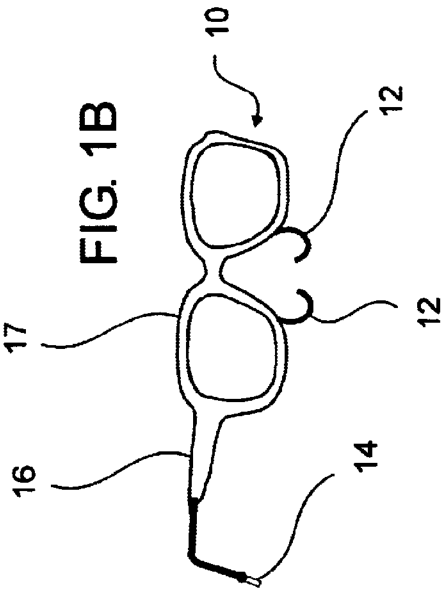
Figure 1C:
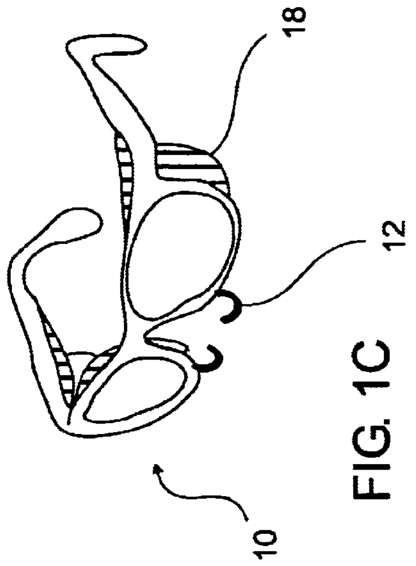
Figure 1A:
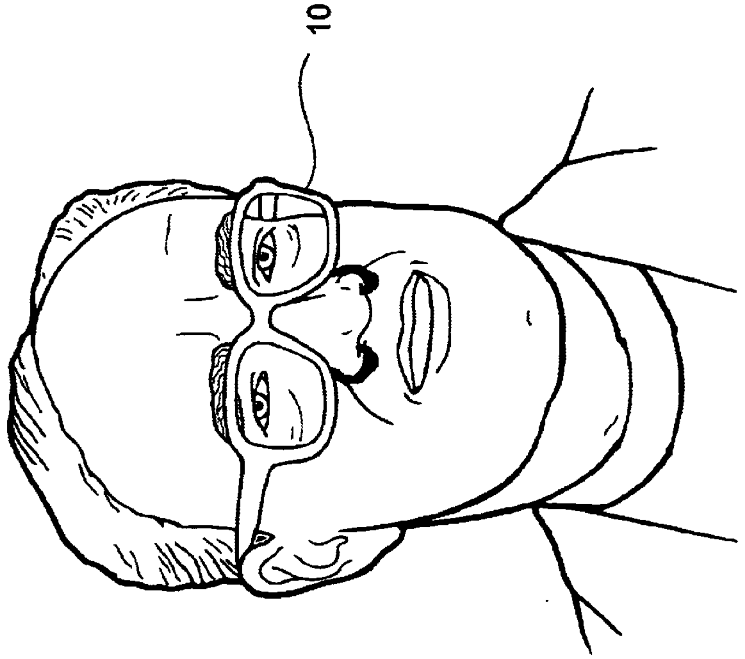

FIG. 1 shows the preferred method of inconspicuously delivering filtered air to the user's nose. Hollow eyeglass frames 10 deliver filtered air from a hose behind the head to nose tubes 12. Nose tubes 12 are small (approximately 1/16 inch) diameter tubes that direct filtered air from the hollow eyeglass frame rims up into the nostrils. These tubes will be molded and colored such that they closely follow and blend in with the contour of the user's face between the frames and the nostrils. Optionally, the user can apply makeup to further hide the nose tubes.

In operation, filtered compressed air is forced through the frames and nose tubes at a flow rate greater than the user's normal peak inhalation rate. That is, the flow rate through the nose tubes is adjusted to be high enough so that some excess filtered air is being exhaled out the nose during normal inhalation. This exhaled filtered air prevents unfiltered outside air from entering the nostrils during inhalation. During user exhalation, all the filtered air will be exhaled as well.

The hollow eyeglass frames and nose tubes form the heart of the preferred embodiment of the present invention and will be offered in a variety of contemporary styles. Since the system is a positive pressure powered system, there is no respiratory stress to the user. Since the mouth is not covered, the system does not interfere with normal conversation. Most importantly, however, the system is completely inconspicuous. From a frontal viewpoint, the short nose tubes are the only visible component of the entire system and should be completely unnoticeable to the casual observer. The user should be able to wear this system in essentially any everyday situation without feelings of self consciousness.

The hollow eyeglass frames and nose tubes may also be useful to oxygen therapy patients that desire an unobtrusive means of oxygen delivery when at work or out and about. Currently, nasal cannula or face masks, which are much more obtrusive, are used for this purpose.

The various components of hollow eyeglass frames 10 are illustrated in FIG. 1B. The respirable air hose is connected to the frames at air inlet port 14. This air port can consist of a short length of small diameter tubing, a short round recess in the temple 16, or any other convenient fitting.

Hollow temples 16 are formed by embedding a metal tube inside plastic temples, molding a hollow channel inside plastic temples, or by using metal tubing to form the metal temple portion of wire frame eyeglasses. Hollow frame rims 17 will be formed in the same manner as the temples. The normal eyeglass hinged joint between temple 16 and frame rims 17 could be eliminated to simplify construction since the user would not typically remove and fold up the eyeglasses in this application. Alternatively, an o-ring or other type seal could be formed at the hinged joint to prevent pressurized respirable air leakage when the eyeglasses are open and in use.

Nose tubes 12 will be formed out of either small diameter disposable metal or plastic tubes and poked into round recesses in the frames rims 17. To keep the system sanitary, old tubes would be pulled out and new tubes inserted periodically. The output ends of nose tubes 12 could optionally be either flared or capped with a porous material to diffuse the high velocity respirable air emanating from the nose tube. This diffusion will reduce or eliminate any feelings of air being blown into the nostrils.

Optionally, a series of one or more small air holes could be placed along the inside of each eye opening in frame rims 17 to fill the space around the eyes between the face and the frames with filtered air. FIG. 1C illustrates shroud 18 that could be optionally added to hollow eyeglass frames 10 to form a partial seal between the frames and the user's face to make this respirable air filling more effective. This filling will displace unfiltered outside air and would be useful to allergy suffers or airline travelers whose eyes are sensitive to pollens or ozone respectively.

Figure 2B:
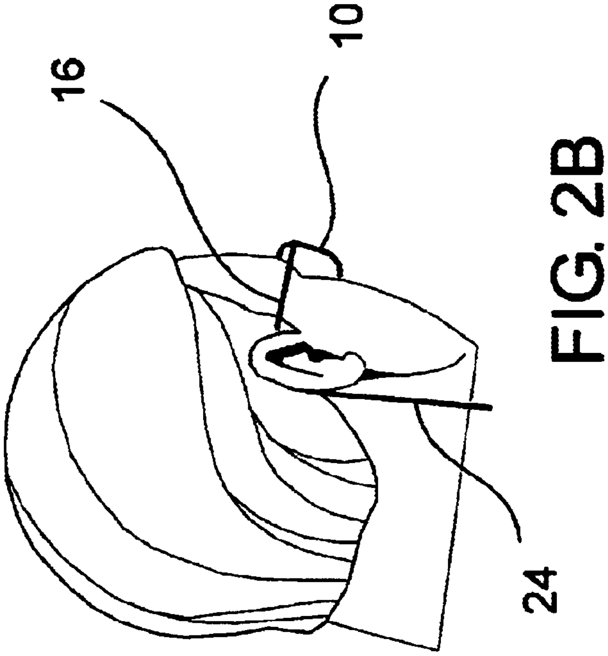
Figure 2A:
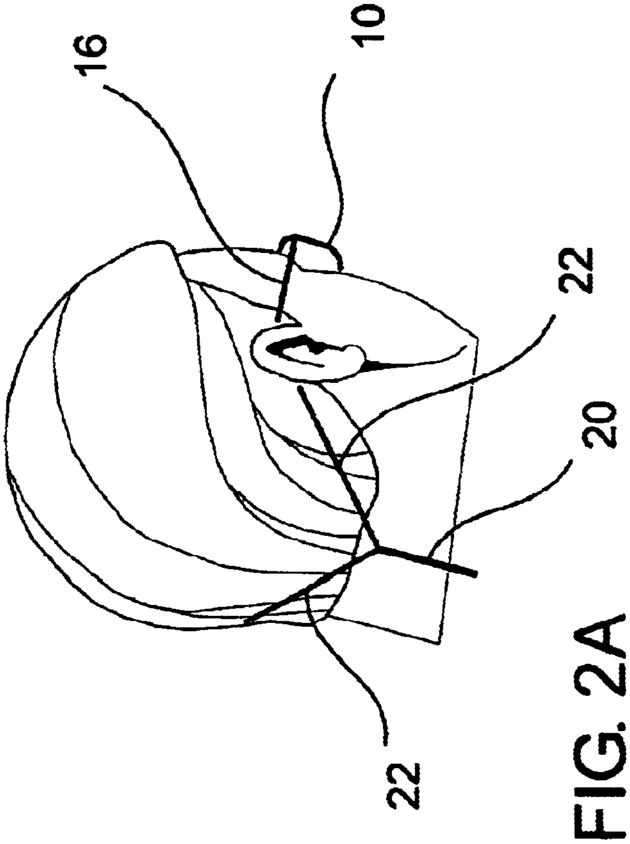

FIG. 2 illustrates the respirable air hose connection to hollow eyeglass frames 10. In FIG. 2A, a small diameter hose 22 is connected to each of the two temples 16. These two separate hoses are then combined into a single slightly larger diameter hose 20 at or below the shirt neckline. Hoses 22 will be designed so that they can be colored and formed to follow the contour of the user's head. The attempt is to make these hoses as inconspicuous as possible. Hose 20 can be of a slightly larger diameter than hose 22 since it will be hidden under the clothing.

In FIG. 2B, an optional arrangement is illustrated in which a single small diameter hose 24 is connected to only one of the temples 16. This arrangement may be even more concealable since only one visible hose is involved. Using a single hose connection only requires one hollow temple but may increase the difficulty of fabricating the hollow frames.

To force sufficient filtered air through the hollow eyeglass frames and small diameter hoses illustrated in FIGS. 1 and 2, an air compressor must be used. Fans and blowers are not capable of producing the approximately 3 to 5 psi air pressure required to achieve the desired flow rates through these small diameter tubes.

Battery powered rotary, diaphragm, and piston type air compressors are readily available in small sizes. However, their form factors are such that they cannot be easily concealed under the clothing. For maximum concealment, the preferred embodiment will use the distributed pump described in FIGS. 3, 4, and 5. This pump achieves the desired pressure and flow rate by combining the output of multiple small compression tubes.

Figures 3A, 3B, 3C:
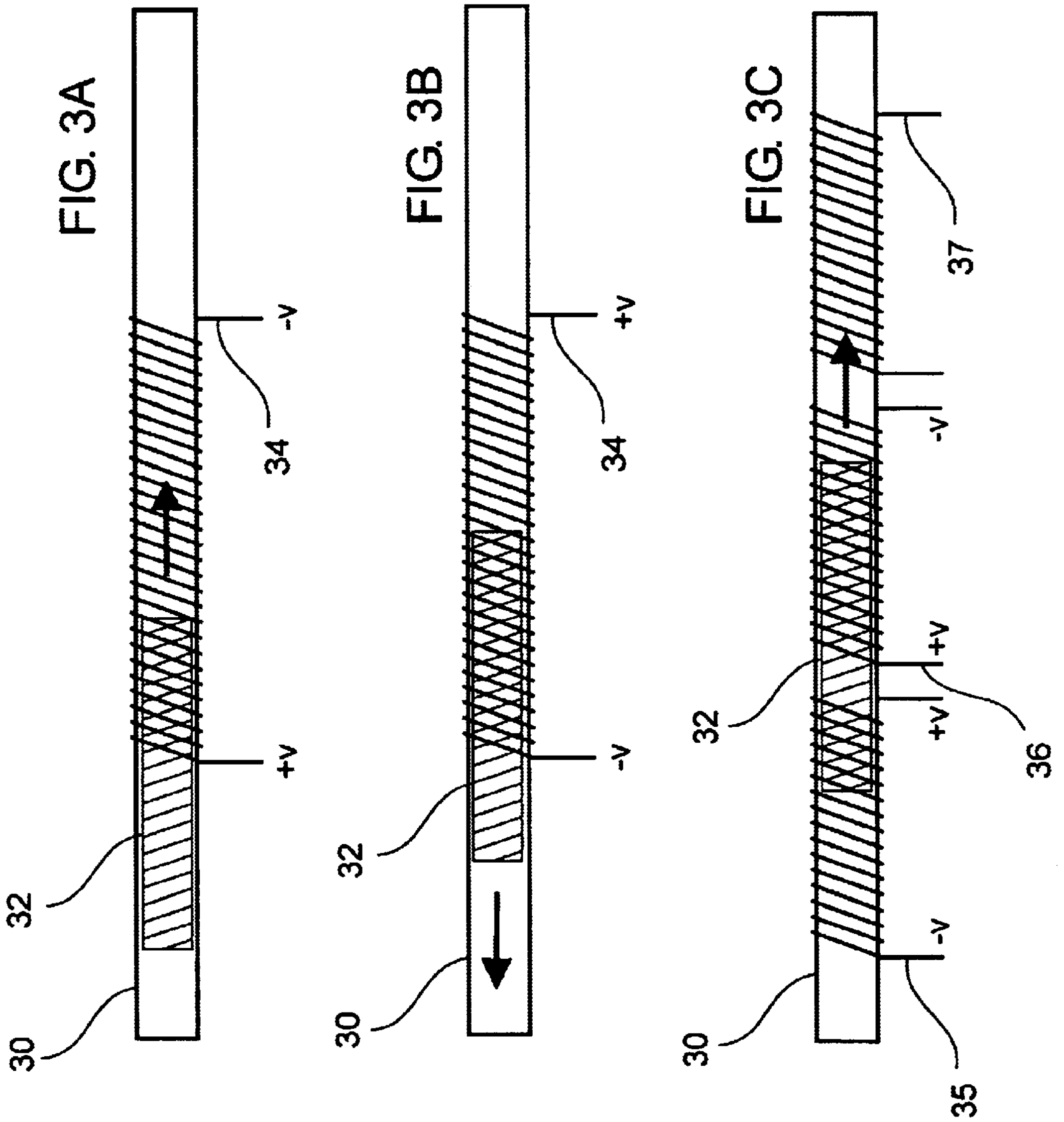

FIG. 3A illustrates the construction of a single compression tube. A ferrous metal piston 32 is inserted into a hollow non-ferrous tube 30 and a wire coil 34 is wound around tube 30. When a voltage is applied as shown, current flows through the coil and creates a magnetic field which forces the piston 32 in the direction shown until it becomes aligned with the center of the coil. The force on the piston is similar to that in an electrical solenoid of similar design.

If the piston 32 is a permanent magnet and inserted into the tube such that its permanent magnetic field is aligned with the coil's magnetic field, the force on the piston is enhanced. If the orientation of piston 32 remains the same but the current flow is reversed by reversing the voltage polarity as shown in FIG. 3B, the piston will be forced out of the coil as shown. Therefore, by alternately reversing the voltage polarity to the coil, the piston can be made to alternately move back and forth inside the tube.

The movement of the piston 32 can be enhanced by winding multiple coils 35, 36, and 37 onto tube 30 as shown in FIG. 3C. When the piston is in the position illustrated in FIG. 3C, coil 35 pushes the piston out of the coil while coil 36 pulls the piston into the coil. Coil 37 is not currently energized so it has no effect on the piston. If, when the piston passes through the center of coil 36, coil 37 is energized to the polarity of coil 36 and coil 36 is energized to the polarity of coil 35, the piston will be forced further on towards the center of coil 37. Coil 35 can be de-energized since the piston is no longer near it.

It should be obvious to anyone skilled in the art that the piston 32 can be made to efficiently oscillate back and forth by selectively applying the proper voltage to the proper coil at the proper time. This piston movement will compress the air ahead of it thus forming an air compressor. Additionally, a voltage will be induced into the unused coils due to the generator effect of moving a magnet in the vicinity of a coil of wire. This induced voltage could be used by electronic control circuitry to sense the position of the piston and activate the proper coil with the proper polarity at the proper time so as to maximize the efficiency of the piston pumping action.

There are many tradeoffs between tube diameter, length, piston material, number of coils, and drive circuit complexity as anyone skilled in the art can appreciate. In general, however, higher pressures can be obtained by using smaller diameter pistons since the air pressure exerted on a smaller diameter cross section is less. Larger air flows can be obtained using a longer stroke (longer tube) and more tubes.

Since it is impractical to wind multiple separate coils onto multiple tubes, the coil arrangement illustrated in FIG. 4 will be used. FIG. 4A shows a length of multiple-wire cable 40 such as ribbon or flex cable. Ribbon cable is constructed by molding many separate parallel wires together. Flex cable is constructed by printing many separate parallel wires onto flexible material such as plastic film using printed circuit techniques. Both types of cable are used extensively in the computer and electronic industries.

FIG. 4B shows an end view of a section of multiple-wire cable 40 that has been folded in half lengthwise. By connecting adjacent wires together in multiple-wire cable 40 using short lengths of wire 42 and applying a voltage as shown, a single energized coil is formed as was formed in FIG. 3A and 3B. By only connecting small groups of adjacent wires together and applying a voltage to each group, multiple energized coils can be formed as was formed in FIG. 3C.

FIG. 4C shows a side view of a series of compression tubes 30 set side by side. Two separate lengths of multiple-wire cables 44 and 46 are sandwiched together and passed around the tubes as shown starting from the left and proceeding to the right. At the right end, the top cable 44 is folded back across the top of the series of compression tubes 30 while the bottom cable 46 is folded back across the bottom of the compression tubes. The two ends of multiple-wire cable 44 are then wired together as in FIG. 4B as are the two ends of multiple-wire cable 46. Again, multiple coils can be formed in both 44 and 46 by only connecting small groups of adjacent wires together.

FIG. 4C shows the current flow in each of the two multiple-wire cables 44 and 46 when the voltage applied is as illustrated. Note that the current flow around compression tube 30 marked "A" due to the current flow in cable 44 is counterclockwise. The current flow around "A" due to multiple-wire cable 46 is zero because equal and opposite currents flow only on one side of tube "A". Likewise, the current flow around compression tube 30 marked "B" due to the current flow in multiple-wire cable 46 is clockwise. The current flow around "B" due to multiple-wire cable 44 is again zero because equal and opposite currents flow only on one side of tube "B". Therefore, the force on the piston in compression tube "A" will be opposite that on the piston in compression tube "B" as was illustrated in FIGS. 3A and 3B.

To construct the distributed pump, the multiple-wire cables 44 and 46 will be wired together and energized by terminating them in printed wiring boards (PWBs). That is, control circuitry and coil driver electronics will be implemented using standard PWB assembly techniques and the final output current will be directed to the multiple-wire cable via circuit traces on the PWB. Using multiple-wire cable to implement the compression tube coils makes the coil wiring economical and easy to manufacture. Using microcontrollers or digital signal processor (DSP) circuits, complex control algorithms can be also easily implemented to optimally drive the compression tube coils.

Figures 5A, 5B:
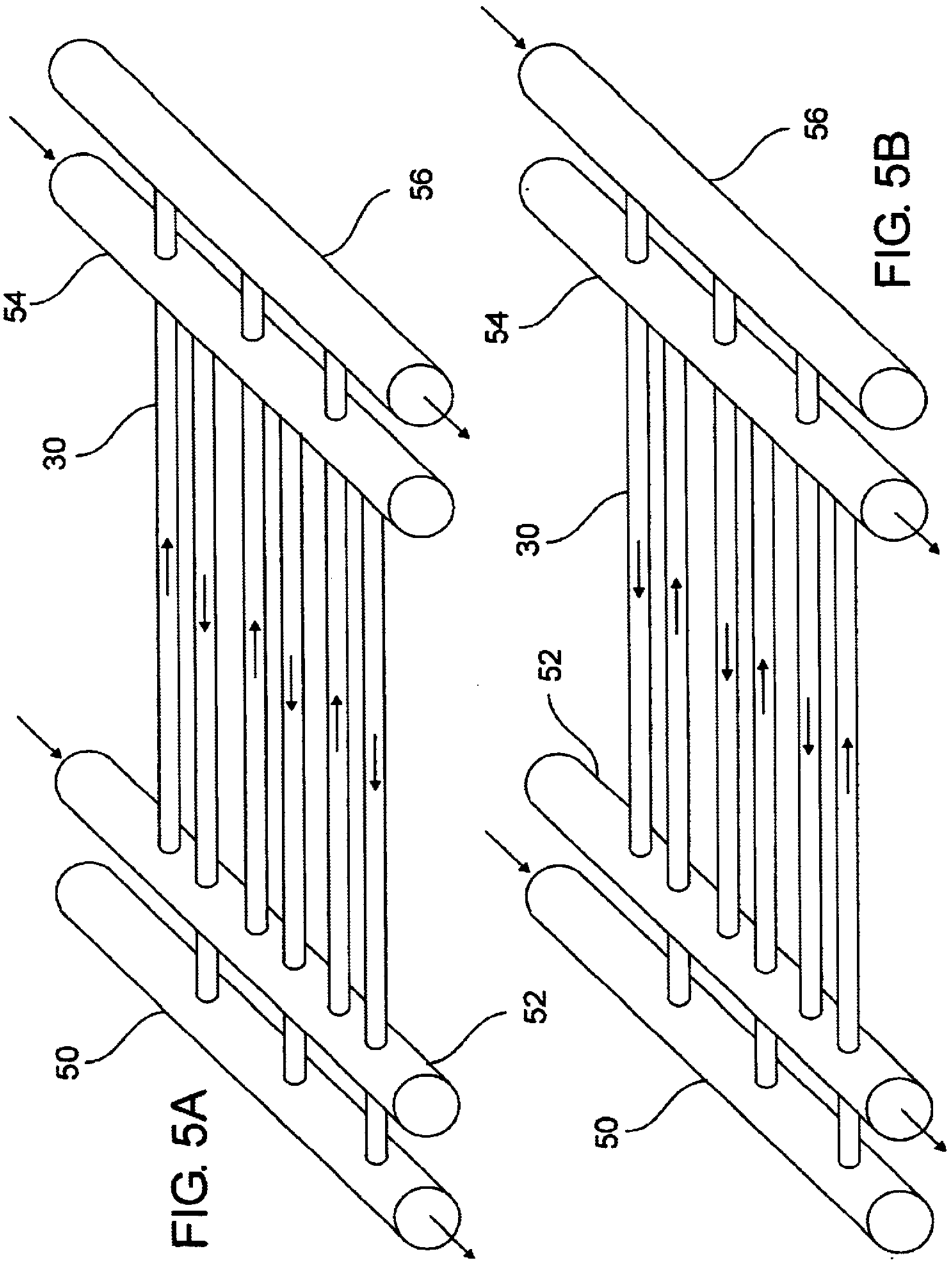

FIG. 5 illustrates how the series of compression tubes 30 are connected together to form the distributed pump. FIG. 5A shows the instantaneous direction of the pistons and air flow for one polarity of the energizing voltage while FIG. 5B shows it for the opposite polarity. Multiple-wire cable is passed through the compression tubes 30 as was shown in FIG. 4C but is not illustrated in FIG. 5 for clarity.

In FIG. 5A, air hose 52 terminates the left end of every other compression tube 30. The remaining tubes pass through air hose 52 and are terminated in air hose 50. A similar arrangement occurs on the right end of the compression tubes where every other tube is terminated in air hose 54 while the remaining tubes pass through 54 and are terminated in hose 56. On the cycle illustrated in FIG. 5A, compressed air from compression tubes 30 flow into air hoses 50 and 56 while new air is drawn into compression tubes 30 via air hoses 52 and 54.

FIG. 5B shows the air flow on the next cycle where compressed air now flows in air hoses 52 and 54 while new air is drawn in through air hoses 50 and 56.

To complete the distributed pump, all that is required is to connect the near end of air hoses 50, 52, 54, and 56 together through one-way air check valves to form the pump high pressure air outlet side. Likewise the far end of air hoses 50, 52, 54, and 56 are connected together through one-way air check valves to form the low pressure air inlet side.

The plurality of compression tubes 30 constitute the compression tube assembly. This assembly is connected to air hoses 50 and 52 which constitute a first air collection duct assembly and to air hoses 54 and 56 which constitute a second air collection duct assembly. These first and second air duct assemblies will be molded or otherwise constructed out of flexible tubing. Both these air duct assemblies and multiple-wire cable wiring assemblies will be flexible enough to allow the distributed pump to be bent lengthwise sufficiently enough to be worn around the waist.

Using the techniques illustrated in FIGS. 3 through 5, an economical distributed pump can be formed that is thin enough to be concealed under the clothing. Pump noise and vibration should be minimal because pistons in adjacent compression tubes are moving in opposite directions which will cause the piston momentum forces in adjacent tubes to cancel.

Figure 6:
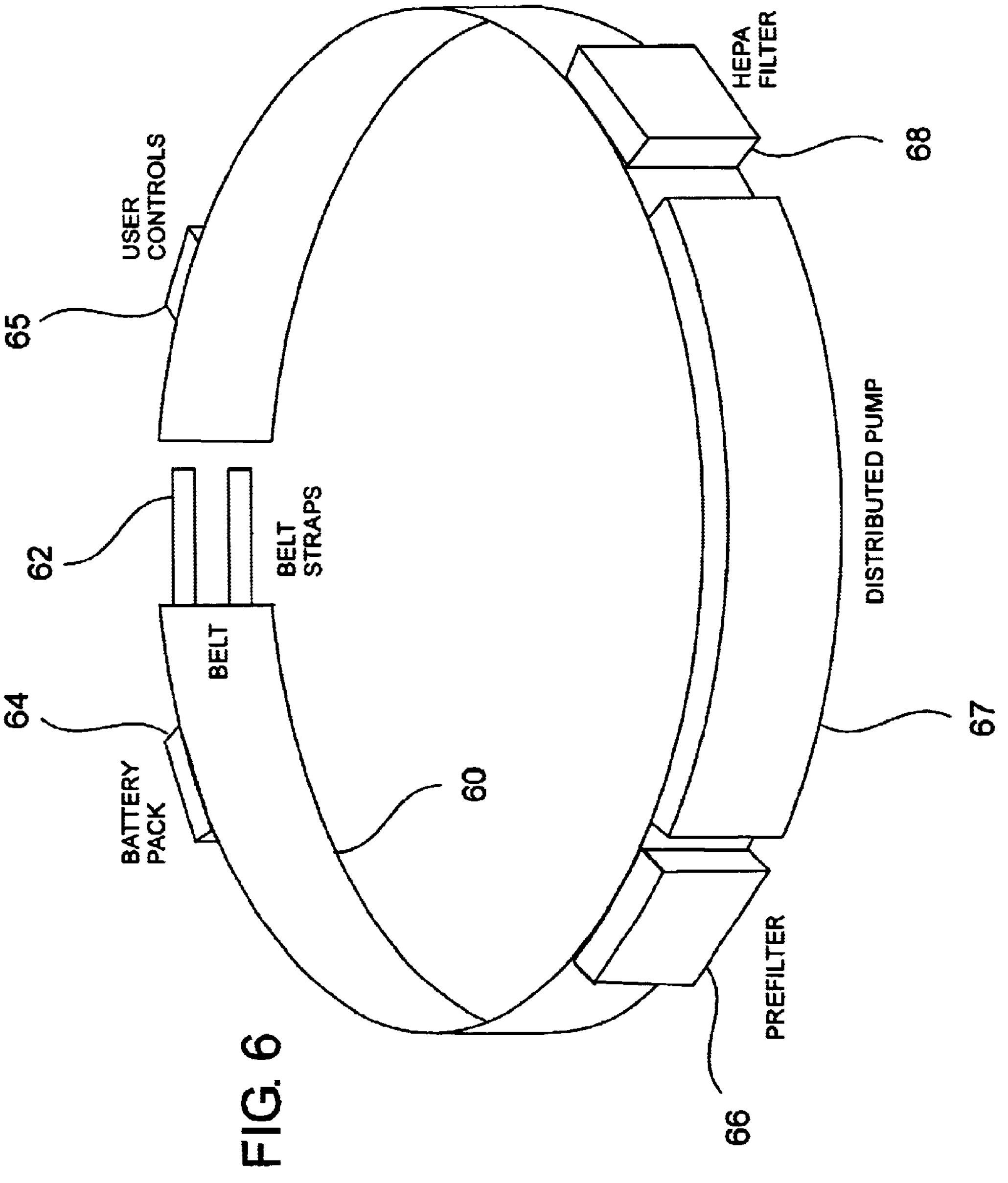

FIG. 6 illustrates the belt mounted air filtration system in its simplest configuration. Hose and wiring connections between the components are not illustrated. Belt 60 is anticipated to be a few inches wide and less than a half inch thick when the components are mounted. It will be worn around the user's waist and fastened using belt straps 62. Belt straps 62 can be standard hook-and-loop fasteners or the like.

Outside air is drawn in through the prefilter 66 by the distributed pump 67 and then forced through HEPA filter 68. Battery pack 64 supplies power to the pump. User controls 65 contains a pump off/on switch and a pump speed control. The speed control allows the user to increase or decrease the filtered air output rate to the nostrils.

The air filtration system of the present invention is designed to be easily configurable so as to support a variety of different filtering applications. Standard filter modules will be provided which the user can connect in series to achieve the filtering goals. FIG. 7 illustrates a few of the standard filter modules that will be provided.

Figure 7B:
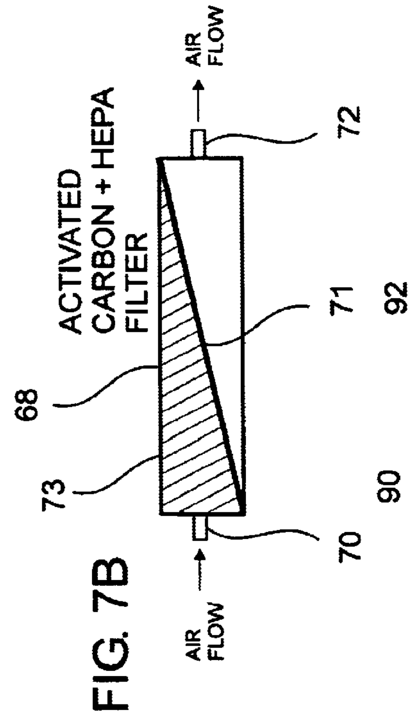
Figure 7D:
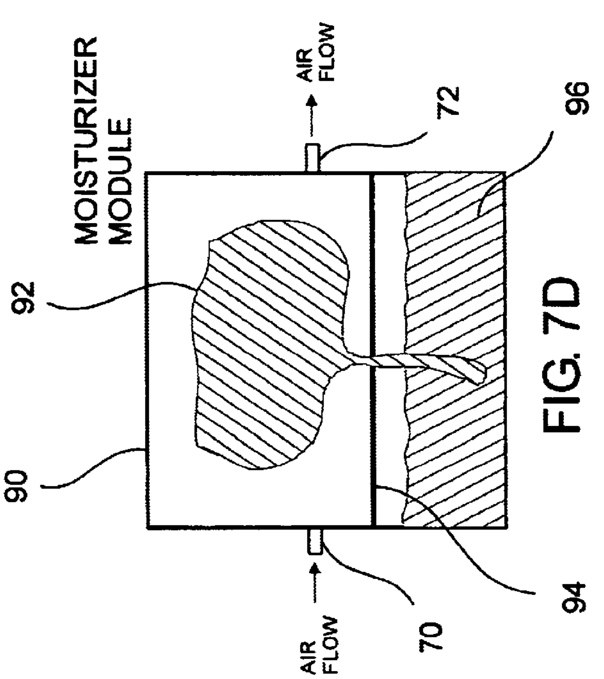
Figure 7A:
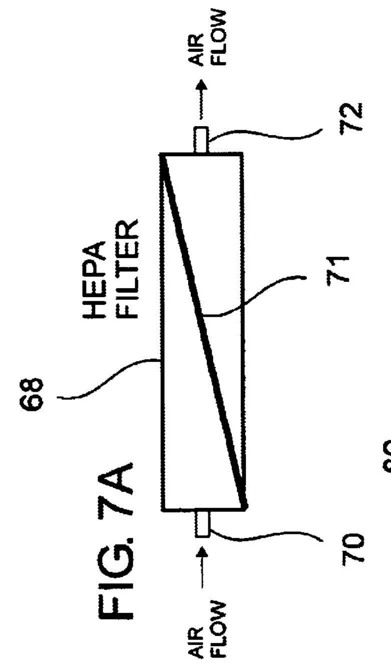

FIG. 7A shows a top view of HEPA filter module 68. HEPA filters are made of submicronic glass fibers in a thickness and texture very similar to blotter paper. They have a minimum particle removal efficiency of 99.97% for all particles of 0.3 micron diameter with higher efficiencies for both larger and smaller particles. Also available are ultra-HEPA filters with even higher efficiencies. Both HEPA and ultra-HEPA filters essentially remove all common airborne pollens and other airborne particulates.

HEPA filters are highly restrictive to airflow compared to standard low efficiency air filters so normally a large surface area must be used when fan and blower type air movers are used. In the present invention, an air compressor is used which allows the use of a small filter because filter air restriction is not as great a problem with air compressors as it is with fans or blowers.

In FIG. 7A, a small HEPA filter 71 is mounted such that it forms a seal between the inlet air port 70 and outlet air port 72. All air entering the HEPA filter module 68 must pass through the HEPA filter 71.

The HEPA filter module 68 also acts as a filtered air accumulator which smoothes out the pump pressure pulses. That is, module 68 stores up air from multiple pump cycles in the same manner as does the air tank on an air compressor.

In FIG. 7B, activated carbon granules or other adsorbent 73 is added to the inlet side of HEPA filter module 68. Activated carbon is very effective for absorbing odors and for eliminating ozone. Another effective absorbent is cpz which is a mixture of carbon, permanganate, and zeolite.

Figure 7C:
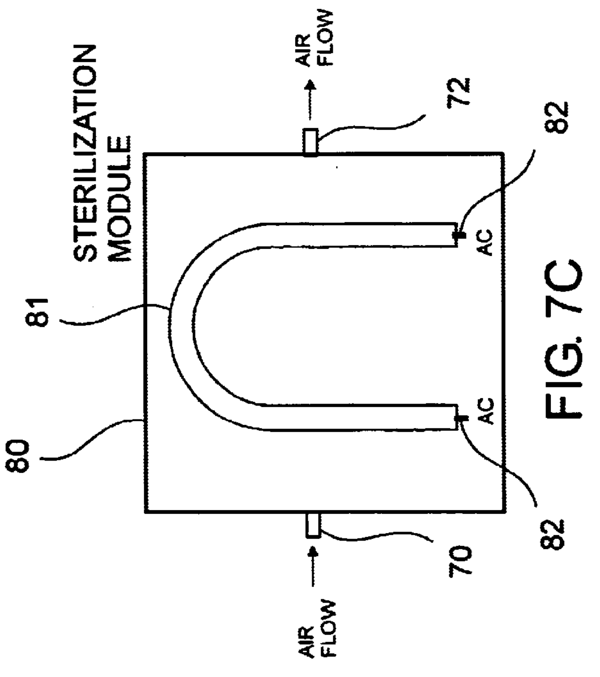

FIG. 7C shows a cross section of sterilization module 80 which contains a germicidal lamp 81 whose input terminals 82 are powered by an AC power source. Germicidal lamps are low-pressure mercury-arc ultraviolet lamps that radiate at 253.7 nm wavelength. Light at this wavelength has an extremely high sterilization effectiveness on bacteria, viruses, yeasts and molds. It is used extensively in air and water purification applications. Germicidal lamps are available in many different sizes, powers, and shapes. A size and power appropriate for the filtered air flow rate required in the present invention will be selected.

FIG. 7D shows a cross section of a moisturizing module 90 containing distilled water 96. Water wick 92 absorbs distilled water 96 and humidifies the filtered air entering through air inlet port 70 and exiting through air outlet port 72. Rigid wall 94 contains a small diameter hole through which wick 92 is passed down and into distilled water 96. Rigid wall 94 only allows water to enter the upper air chamber via absorption through wick 92.

The air filtration system of the present invention is designed to support a variety of different filtering applications by series connecting various filtering modules together. In its most unobtrusive and concealable embodiment, the hollow eyeglass frames and the distributed pump will be the primary components used.

However, other useful embodiments of the system will also be offered. For example, in a hospital patient application, a bedside mounted unit would be more desirable than a portable belt mounted unit. For an airline traveler, a small travel packaged unit that could be carried in a brief case, and only used during the flight, might be more desirable than a wearable system.

Figure 8:
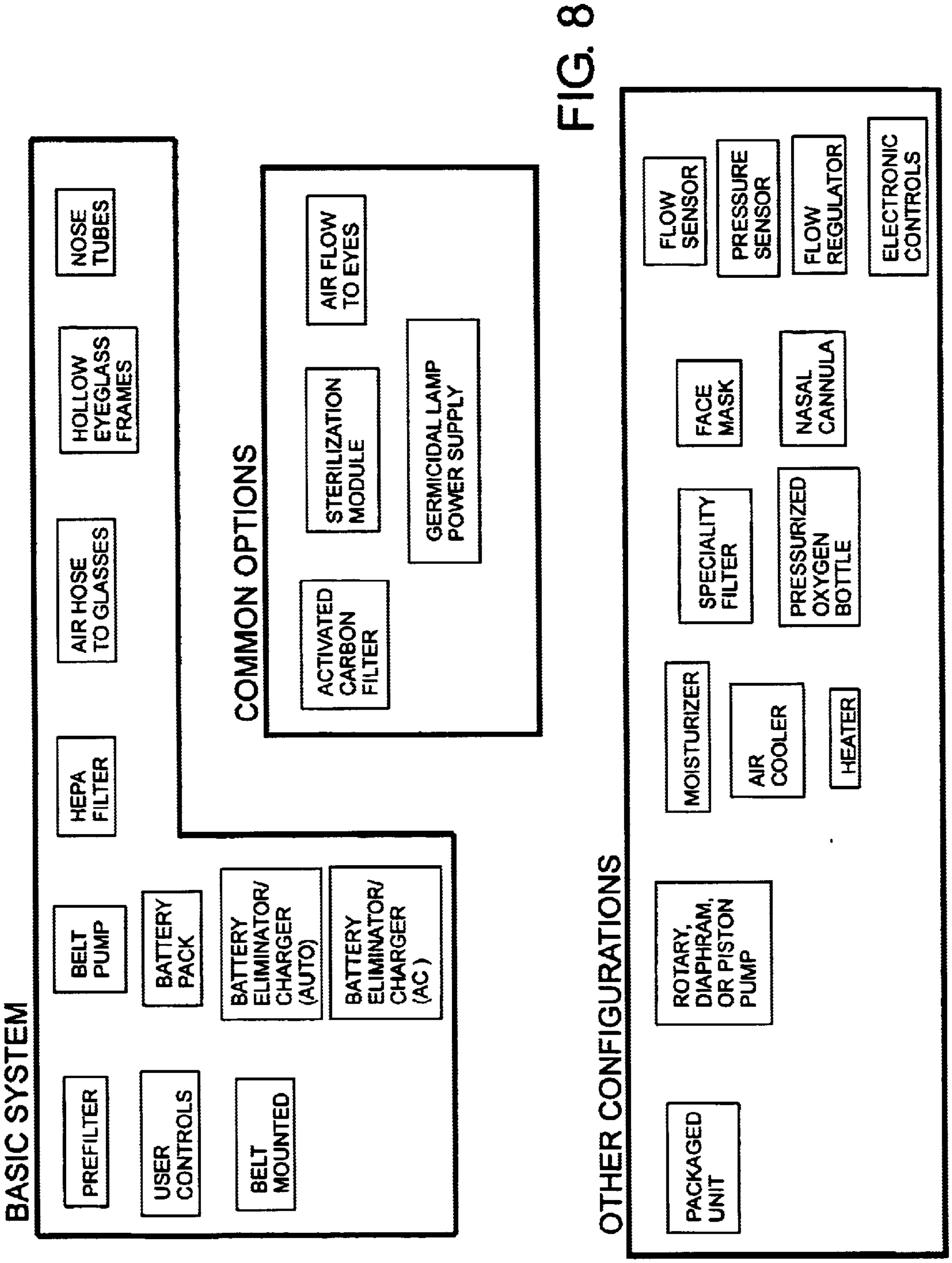
FIG. 8 is a block diagram of the various components that can be used to make up different configurations of the system.

FIG. 8 lists in block diagram form some of the various system components that could be used to provide various configurations of the air filtration system.

In the most basic belt mounted configuration, a prefilter is used to filter all large dust particles out of the input air so as to protect the pump. Typically, low or moderate efficiency air filters are used for this purpose to reduce filter air flow restriction when fans or blowers are used. Since an air compressor is used in the present invention, filter air flow restriction is not as great a problem. Therefore, either a moderate efficiency filter or a HEPA filter will be used for the prefilter. The construction of this filter will be similar to that illustrated in FIG. 7A.

Battery eliminators will be offered to prevent belt mounted battery drain and to charge the belt mounted battery while traveling in a car, sitting at a desk, etc.

The most common options for the belt mounted system are anticipated to be the activated carbon filter, sterilization module, and air flow to the eyes. When using the sterilization module, a separate power supply module may be required to operate the germicidal lamp.

In the packaged configuration, a readily available rotary, diaphragm, or piston pump may be used instead of the distributed pump. These pumps could also be used in place of the distributed pump on all or some of the belt mounted configurations if they are found to offer some advantage over the distributed pump.

The moisturizer module may be useful in dry conditions to keep from drying out the nose tissues. The air cooler module may be required to remove germicidal lamp heat from the air stream when using the sterilization module. It will be constructed using solid state thermoelectric cooler devices. The heater module will be constructed using a resistive heating element. The heater and cooler may be useful in either extremely cold or hot environments respectively or for asthma patients who cannot tolerate rapid air temperature variations. The heater and cooler modules will be thermo-statically controlled to automatically maintain the temperature selected by the user.

For painting or industrial applications, other specialty filter modules will be offered. Commercial filters are readily available for a wide variety of organic and chemical vapors. These existing filter technologies will be repackaged into modules compatible with the belt mounted system. For industrial applications, half and full face masks will be provided to be used with the belt mounted air filtration system.

Nasal cannula devices will also be offered with the bedside and travel packaged systems. Nasal cannulas are commonly used to administer oxygen through the nose to pilots and to patients. They are clipped or otherwise conveniently attached to the nose and would be useful for hospital patients or for travelers sleeping in musty hotels.

For some applications, the additional complexity of a flow regulator system may be desired. A flow regulator system would avoid wasting filtered air during exhalation which would allow a smaller pump to be used and would extend filter and battery life. It would also make breathing more natural and would eliminate any sensation of air being blown into the nose.

Standard flow regulator systems use a pressure regulator valve that allows air to flow to the user as soon as a slight negative inhalation pressure is encountered. The design of these systems is straight forward but their use requires that the nostrils be plugged with a one-way exhalation check valve. That is, upon inhalation, the nose check valve would close and all inhalation air would be supplied by the nose tubes due to the negative inhalation pressure. Upon exhaling, the check valve would open and air would be exhaled out the nose. The slight positive exhalation pressure would close the pressure regulator valve and shut off air flow through the nose tubes.

A flow regulator system could also be provided that does not require the nostrils to be plugged. This system would consist of a flow sensor, pressure sensor, flow regulator, and electronic control circuitry. The flow sensor would detect air speed and direction inside the nose. The pressure sensor would regulate the pump speed to maintain a constant pressure in the filtered air accumulator provided by the HEPA filter module. A flow regulator would instantaneous adjust the filtered air output pressure to the nose tubes on commands from the electronic control circuitry.

The flow regulator system would adjust the instantaneous pressure to the nose tubes to always maintain some minimal exhaled air flow out the nose. That is, during exhalation, the filtered air flow would be completely cut off thus conserving filtered air from the accumulator. During inhalation, the filtered air flow would be increased to that required for both user inhalation and to exhale some additional air so as to prevent any outside unfiltered air from being inhaled.

Figure 9:
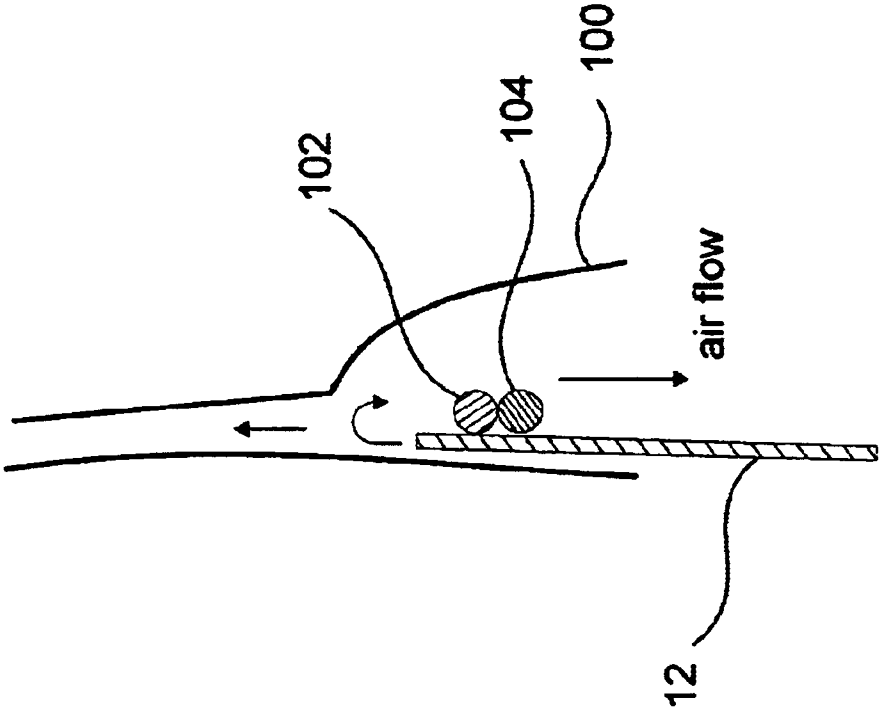
FIG. 9 illustrates a flow sensor mounted on a nose tube and positioned inside a nostril.

FIG. 9 illustrates the preferred embodiment of the flow sensor. Small matched thermistors 102 and 104 are positioned together on nose tube 12 paralleled to the air flow inside nostril 100 as shown in FIG. 9. The resistance of each thermistor will be measured as a small current is passed through them. Since the resistance of a thermistor varies with temperature, the thermistor's temperature can be determined from its resistance.

The small current passed through the thermistors cause them to self heat slightly while air flow through the nostrils causes them to cool slightly. Since the two thermistors are positioned close together and parallel to the air flow, the air flow to the downstream thermistor 104 is partially blocked by the upstream thermistor 102 and therefore runs hotter because it receives less cooling air than the upstream thermistor 102.

The differential resistance of the two thermistors indicates the direction and velocity of air flow in the nostril and can be used by the control circuitry to adjust the nose tube flow rate to always exhale some air out the nostrils. Other types of temperature sensors, such as semiconductor sensors, can be used instead of thermistors. Wiring for the sensors will be embedded in the nose tubes, hollow eyeglass frames, and air hose to the belt pack where the electronic control circuitry will reside.

Although the preferred embodiments of the invention have been illustrated and described in detail, it will be readily apparent to those skilled in the art that various modifications may be made therein without departing from the spirit of the invention.

What is claimed is:

1. An inconspicuous positive pressure powered air purifying delivery system for supplying respirable air to the nostrils of an individual comprising:

a. an air compressor for converting ambient air to pressurized air at a predetermined pressure and flow rate;

b. a filter for converting said pressurized air to pressurized respirable air;

c. hollow eyeglass frames defining air ducts between one or more air inlet ports positioned at or near the end of one or both temples, and one or more air outlet ports extended alongside the nose and directed towards the nostrils, so as to direct air into the nostrils of an individual; and d. flexible tubing to connect said pressurized respirable air to said hollow eyeglass frames inlet ports;

whereby said respirable air is delivered to the nostrils of an individual.

2. An inconspicuous positive pressure powered air purifying delivery system as in claim 1 further including nose tubes connected to said hollow eyeglass frames outlet ports, said nose tubes extended alongside the nose and directed towards the nostrils, so as to direct air into the nostrils of the individual.

3. An inconspicuous positive pressure powered air purifying delivery system as in claim 1 further including a plurality of small air outlet holes around the inner frame rim surface of said hollow eyeglass frames.

4. An inconspicuous positive pressure powered air purifying delivery system as in claim 3 further including a shroud that essentially encloses the space between the inner frame rim surface of said hollow eyeglass frames and the individual's face.

5. An inconspicuous positive pressure powered air purifying delivery system as in claim 1 wherein said filter is designed to remove particulates.

6. An inconspicuous positive pressure powered air purifying delivery system as in claim 1 further including a conditioner for sterilizing, humidifying, heating, or cooling said pressurized respirable air.

7. An inconspicuous positive pressure powered air purifying delivery system as in claim 1 further including a conditioner, for sterilizing said pressurized respirable air, utilizing germicidal ultra-violet lamps.

8. An inconspicuous positive pressure powered air purifying delivery system as in claim 1 wherein said air compressor includes electric motor powered rotary, diaphragm, or piston type air compressors.

9. An inconspicuous positive pressure powered air purifying delivery system as in claim 1 wherein said air compressor includes a distributed pump comprising:

a. a compression tube assembly having a first end and a second end, wherein said compression tube assembly includes a plurality of compression tubes arranged substantially parallel to each other and extending between said first and second ends of said compression tube assembly, and wherein each of said compression tubes has a piston therein;

b. a first air collection duct assembly coupled to said first end of said compression tube assembly, said first air collection duct assembly having a first check valve arranged to allow air passage into said first air collection duct assembly and a second check valve arranged to allow air passage out of said first air collection duct assembly;

c. a second air collection duct assembly coupled to said second end of said compression tube assembly, said second air collection duct assembly having a first check valve arranged to allow air passage into said second air collection duct assembly and a second check valve arranged to allow air passage out of said second air collection duct assembly;

d. at least one multiple-wire cable intertwined around said compression tubes of said compression tube assembly; and e. a control circuit coupled to said at least one cable and configured to supply current to said at least one cable, said current being configured to propel said pistons, with pistons in adjacent ones of said compression tubes being propelled in opposing directions.

10. An inconspicuous positive pressure powered air purifying delivery system as in claim 1 further including a user control module for controlling the flow rate of said pressurized respirable air.

11. An inconspicuous positive pressure powered air purifying delivery system as in claim 1 further including a battery pack for portable operation.

12. An inconspicuous positive pressure powered air purifying delivery system as in claim 1 further including means for securing system components to an individual wherein said securing means comprises:

a. a belt to be worn around the waist of an individual; and b. component attachment means for allowing various combinations and types of filter, conditioner, compressor, battery, and user control devices to be modularly mounted on said belt and connected together.

13. An inconspicuous positive pressure powered air purifying delivery system as in claim 1 wherein said flow rate is selected to ensure that some said respirable air is always expelled from the nostrils during all phases of the individual's respiration cycle.

14. An inconspicuous positive pressure powered air purifying delivery system as in claim 1 further including a flow regulator system comprising:

a. flow sensor means mounted on said air outlet port near the nostrils for measuring air flow velocity out of the nostrils; and b. flow regulator means to modulate the flow rate to maintain a predetermined air flow velocity out of the nostrils.

15. An inconspicuous positive pressure powered air purifying delivery system as in claim 14 wherein said flow sensor includes two matched thermistors positioned close together on said nose tube and parallel to the air flow inside the nostril, wherein current is passed through said thermistors, and said air flow velocity is determined by measuring the differential resistance of the two thermistors.

16. An inconspicuous positive pressure powered air purifying delivery system as in claim 1 wherein said respirable air includes oxygen from a pressurized container.

17. A pair of eyeglasses for inconspicuously delivering respirable air to the nostrils of an individual comprising hollow eyeglass frames defining air ducts between one or more air inlet ports and one or more air outlet ports.

18. A pair of eyeglasses for inconspicuously delivering respirable air to the nostrils of an individual as in claim 17 wherein said air inlet ports are positioned at or near the end of one or both temples.

19. A pair of eyeglasses for inconspicuously delivering respirable air to the nostrils of an individual as in claim 17 wherein said air outlet ports are extended alongside the nose and directed towards the nostrils so as to direct air into the nostrils of the individual.

20. A pair of eyeglasses for inconspicuously delivering respirable air to the nostrils of an individual as in claim 17 further including nose tubes connected to said air outlet ports, said nose tubes extended alongside the nose and directed towards the nostrils so as to direct air into the nostrils of the individual.

21. A pair of eyeglasses for inconspicuously delivering respirable air to the nostrils of an individual as in claim 20 wherein said nose tubes are removable.

22. A pair of eyeglasses for inconspicuously delivering respirable air to the nostrils of an individual as in claim 17 further including a plurality of air outlet holes around the inner frame rim surface of said hollow eyeglass frames.

23. A pair of eyeglasses for inconspicuously delivering respirable air to the nostrils of an individual as in claim 22 further including a shroud that essentially encloses the space between the inner frame rim surface of said hollow eyeglass frames and the individual's face.

24. A wearable distributed air pump for supplying pressurized air to an air respirator, said air pump comprising:

a. a compression tube assembly having a first end and a second end, wherein said compression tube assembly includes a plurality of compression tubes arranged substantially parallel to each other and extending between said first and second ends of said compression tube assembly, and wherein each of said compression tubes has a piston therein;

b. a first air collection duct assembly coupled to said first end of said compression tube assembly, said first air collection duct assembly having a first check valve arranged to allow air passage into said first air collection duct assembly and a second check valve arranged to allow air passage out of said first air collection duct assembly;

c. a second air collection duct assembly coupled to said second end of said compression tube assembly, said second air collection duct assembly having a first check valve arranged to allow air passage into said second air collection duct assembly and a second check valve arranged to allow air passage out of said second air collection duct assembly;

d. at least one multiple-wire cable intertwined around said compression tubes of said compression tube assembly; and e. a control circuit coupled to said at least one cable and configured to supply current to said at least one cable, said current being configured to propel said pistons, with pistons in adjacent ones of said compression tubes being propelled in opposing directions.

25. A wearable distributed air pump for supplying pressurized air to an air respirator as in claim 24 wherein said piston is a permanent magnet.

26. A wearable distributed air pump for supplying pressurized air to an air respirator as in claim 24 wherein said air collection ducts are flexible.

27. A wearable distributed air pump for supplying pressurized air to an air respirator as in claim 24 wherein the wires of said at least one multiple-wire cable are connected to form a plurality of current coils around said compression tube assembly.

28. A wearable distributed air pump for supplying pressurized air to an air respirator as in claim 27 further including processing circuit means for sequentially energizing said plurality of current coils, based on said piston's current position within said compression tube, to obtain maximum pumping efficiency.

29. A method for inconspicuously delivering respirable air to the nostrils of an individual comprising the steps of:

a. providing a source of respirable air at a predetermined pressure and flow rate;

b. piping said respirable air to the vicinity of the back or side of the head using flexible tubing; and c. providing hollow eyeglass frames with an air inlet port and an air outlet port to duct said respirable air from said back or side of the head to the nostrils.

* * * * *